United States Patent
Charlton

(10) Patent No.: US 9,880,090 B2
(45) Date of Patent: Jan. 30, 2018

(54) HPLC REVERSE-FLOW FLOW CELL

(71) Applicant: Bio-Rad Laboratories, Inc., Hercules, CA (US)

(72) Inventor: Chris Charlton, Martinez, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 94 days.

(21) Appl. No.: 14/815,566

(22) Filed: Jul. 31, 2015

(65) Prior Publication Data

US 2016/0047738 A1    Feb. 18, 2016

Related U.S. Application Data

(60) Provisional application No. 62/037,737, filed on Aug. 15, 2014.

(51) Int. Cl.
| | |
|---|---|
| *G01N 21/00* | (2006.01) |
| *G01N 21/05* | (2006.01) |
| *G01N 30/74* | (2006.01) |
| *G01N 21/09* | (2006.01) |
| *G01N 21/64* | (2006.01) |

(52) U.S. Cl.
CPC ............ *G01N 21/05* (2013.01); *G01N 30/74* (2013.01); *G01N 21/09* (2013.01); *G01N 2021/6467* (2013.01); *G01N 2030/746* (2013.01)

(58) Field of Classification Search
CPC ..... G01N 2021/6467; G01N 2030/746; G01N 21/05; G01N 21/09; G01N 30/74; B60K 2350/1004; G06F 3/04883; G06K 9/18
USPC .................................................. 356/432–444
See application file for complete search history.

(56) References Cited

U.S. PATENT DOCUMENTS

| | | | |
|---|---|---|---|
| 2005/0163662 A1* | 7/2005 | Mueller | G01N 21/05 422/68.1 |
| 2006/0068490 A1* | 3/2006 | Tang | B01F 5/0603 435/287.2 |
| 2014/0083173 A1* | 3/2014 | Rapp | B01L 3/502715 73/61.59 |

FOREIGN PATENT DOCUMENTS

| | | |
|---|---|---|
| EP | 1219962 A1 | 7/2002 |
| EP | 1522849 A1 | 4/2005 |

OTHER PUBLICATIONS

EP15180207.1, "Extended European Search Report", dated Dec. 9, 2015, 10 pages.

* cited by examiner

*Primary Examiner* — Tri T Ton
(74) *Attorney, Agent, or Firm* — Kilpatrick Townsend & Stockton LLP

(57) ABSTRACT

Improved flow cells, as well as systems and methods for using the improved flow cells, are provided.

15 Claims, 8 Drawing Sheets

HPLC REVERSE-FLOW FLOW CELL

CROSS-REFERENCE TO RELATED PATENT APPLICATIONS

The present application claims benefit of priority to U.S. Provisional Patent Application No. 62/037,737, filed Aug. 15, 2014, which is incorporated by reference.

BACKGROUND OF THE INVENTION

Systems for optical analysis of a test liquid during chromatography generally include a light source, a diffraction grating, filter, or other means for selecting a wavelength, a flow cell to allow interrogation of the test liquid during the chromatographic analysis with the selected wavelength, and a detector. The flow cell must be constructed from materials that are resistant to the solutions encountered in liquid chromatography. To achieve high sensitivity, the flow cell must have a small volume to prevent peak dispersion and a long pathlength. These and other considerations of flow cell design require tradeoffs between sensitivity, throughput, peak resolution, and manufacturability.

BRIEF SUMMARY OF THE INVENTION

In one aspect, the present invention provides a flow cell for optical analysis of a test liquid, the flow cell comprising: —a main body; —a first and a second optical window, the first and second optical windows on opposite sides of the main body; —an inlet for supply of the test liquid into the flow cell, wherein the inlet is configured to supply a vortex flow of the test liquid through the main body when the test liquid is supplied through the inlet and into the flow cell; and —an outlet for discharge of the test liquid from the flow cell, wherein the inlet and outlet are on opposite sides of the main body.

In some embodiments, the main body has a circular cross-section. In some cases, the cross-section of the main body has a larger surface area at the inlet side as compared to the outlet side. In some cases, the measuring chamber (e.g., main body) has a top portion and a bottom portion, wherein the top portion slopes from the inlet to the outlet, thereby decreasing the surface area of the cross-section of the main body. In some cases, the measuring chamber (e.g., main body) has a top portion and a bottom portion, wherein the bottom portion slopes from the inlet to the outlet, thereby decreasing the surface area of the cross-section of the main body. In some cases, the measuring chamber (e.g., main body) has a top portion and a bottom portion, wherein the top portion and the bottom portions slope from the inlet to the outlet, thereby decreasing the surface area of the cross-section of the main body. In some cases, the inlet is configured to supply the test liquid at a tangent relative to (i) an inscribed circle of the inner volume of the main body; or (ii) the circular cross-section of the main body of the flow cell, when the test liquid is supplied through the inlet and into the flow cell.

In another aspect, the present invention provides a system comprising any one of the foregoing flow cells, wherein the system comprises a light detector positioned near the first optical window. In some cases, the light detector is proximal to the inlet. In some cases, the light detector is proximal to the outlet. In some cases, the system comprises an incident light source positioned near the second optical window. In some cases, the system further comprises a pump for pumping the test liquid into the inlet.

In another aspect, the present invention provides a method for optical analysis of a test liquid, the method comprising: supplying the test liquid into the flow cell inlet of any one of the foregoing systems, thereby generating a vortex flow of the test liquid through the measuring chamber (e.g., main body) of the flow cell; optionally, changing the test liquid; and measuring the optical properties of the test liquid(s) by detecting a photon from the flow cell with the light detector. In some cases, the detecting the photon from the flow cell with the light detector comprises detecting a photon emitted from one or more components of the test liquid after stimulation with an incident light source. In some cases, the detecting the photon from the flow cell with the light detector comprises detecting a photon transmitted through the flow cell from the incident light source (e.g., detecting absorbance of photons by the test liquid).

DETAILED DESCRIPTION OF THE INVENTION

I. Flow Cells

Improved flow cells for optical analysis of a test liquid by liquid chromatography (e.g., HPLC) are described herein. Flow cells described herein include those that are designed to introduce liquid through the flow cell main body in a vortex flow. The vortex flow can reduce or eliminate dead zones or areas of recirculation and thus increase the likelihood that a flow cell geometry is well-flushed. Flow cells described herein also include those in which the cross-sectional area of the flow cell main body reduces in the direction from the inlet to the outlet, thereby producing a narrowing internal volume to the flow cell in the direction of liquid flow. This narrowing as liquid traverses from the inlet of the flow cell main body to the outlet can, in some cases, maintain the vortex flow of the liquid through the flow cell main body.

Figure 1:
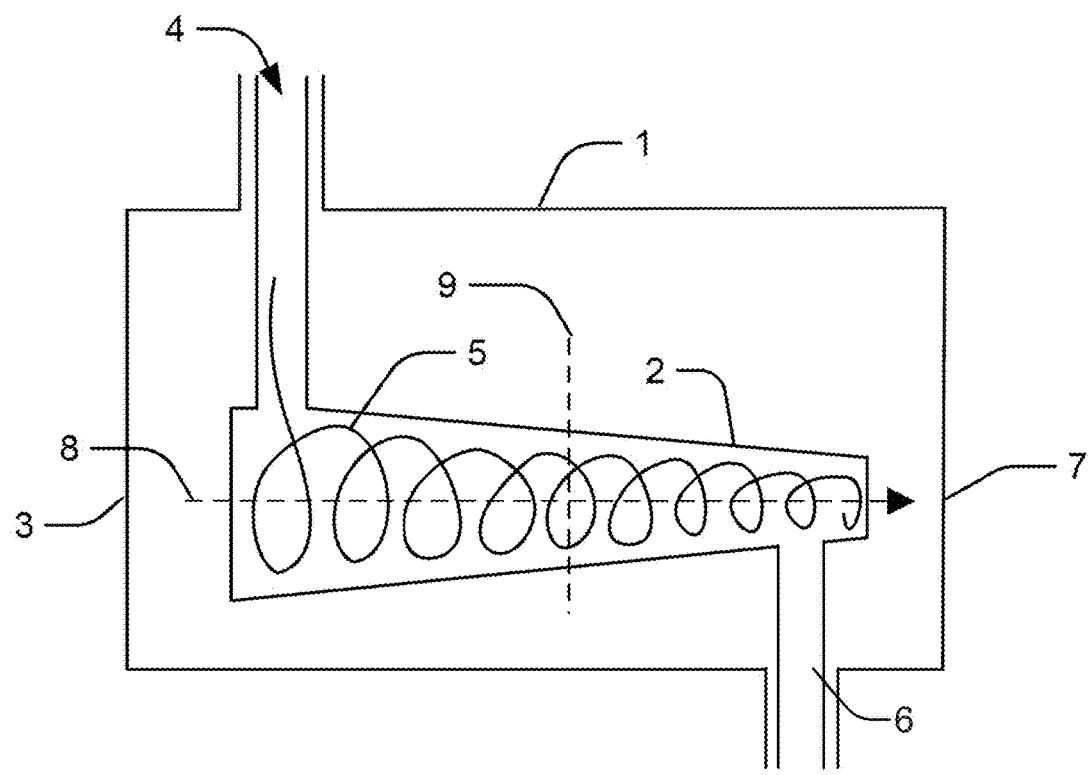
FIG. 1: Depicts a side view of a flow cell described herein. A vortex flow of liquid is introduced via the fluid inlet traversing through the flow cell main body to the outlet.

Aspects of the flow cells as described herein are depicted in FIG. 1. In some embodiments, the flow cell (1) can contain: a main body (2); a first optical window (3); an inlet (4) for supply of the test liquid into the flow cell, wherein the inlet is configured to supply a vortex flow (5) of the test liquid through the main body when the test liquid is supplied through the inlet and into the flow cell; and an outlet for discharge of the test liquid from the flow cell (6). The flow cell can further contain a second optical window (7). Items (8) and (9) represent axes that are respectively parallel and perpendicular to the bulk direction of flow of a test liquid in the flow cell from inlet (4) to outlet (6). A vortex flow (5) results when fluid is forced through the flow cell via the inlet (3).

Figure 2:
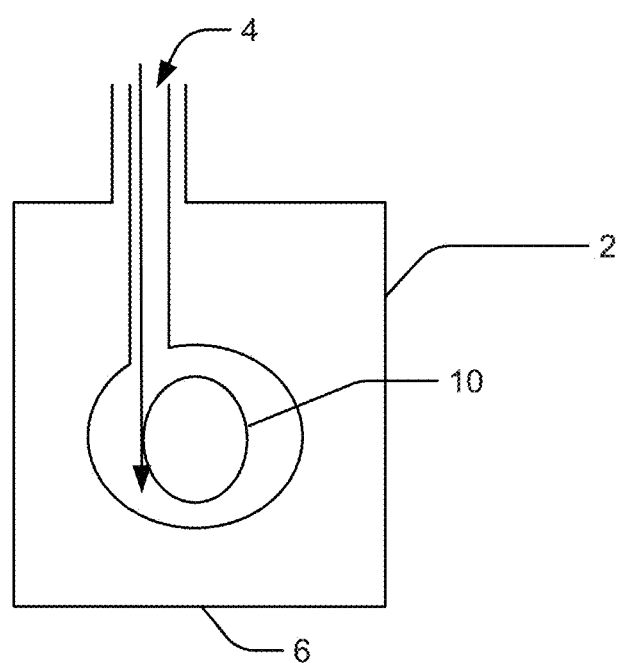
FIG. 2: Depicts a front view of a flow cell of FIG. 1. The inlet introduces liquid at a tangent relative to the circular cross sectional area of the flow cell, thereby generating a vortex flow.

As used herein, the term "vortex flow" refers to a generally to a flow of liquid around an axis. A typical vortex flow in the context of the present invention is depicted in FIG. 1. The vortex flow can be generated, e.g., by introducing the test liquid at a tangent relative to an inscribed circle of the inner volume of the main body. For example, as depicted in FIG. 2 in some cases, the inner volume of the flow cell main body has a circular cross section (10), and the vortex flow is generated by introducing a test liquid at a tangent relative to the circular cross section. The presence or absence of a vortex flow of liquid does not affect the bulk direction of liquid flow through the flow cell, which is from inlet to outlet.

One or more optical windows (3) and (7) can provide for optical interrogation of the test liquid as it resides in, or traverses, the flow cell. In some cases, optical windows are formed of a material that has a larger refractive index than the body of the flow cell. In such cases, the difference in refractive index between the flow cell body and the optical windows can inhibit or eliminate transmission of light into or through the body of the flow cell, thus providing efficient transmission of light through the test liquid. The optical windows should be transparent to the wavelength of light used in the analysis. For example, for analysis of ultraviolet light absorptive properties of the test liquid, the one or more optical windows should be transparent to ultraviolet wavelengths of light. In some cases, the optical windows are polished to increase light transmission efficiency. The optical windows are typically formed of, or coated with, a material that is highly resistant to corrosion. Suitable materials for flow cell optical windows include corundum, glass, borosilicate glass, fused quartz, lithium tantalite, lithium niobate, or a polymer that is transparent at a desired wavelength or range of wavelengths, such as UV transparent polymethylmethacrylate.

In some embodiments, the flow cell contains one optical window. In such cases, the single optical window can be configured to interrogate the photon production properties of the test liquid. For example, the flow cell can be configured in a liquid chromatography system such that the optical window is adjacent, or proximal, to a light detector. Photon production in the test liquid can then be detected by the transmission of photons through the optical window to the light detector. In some cases, such a configuration can analyze luminescence, chemiluminescence, phosphorescence, or luciferase activity of one or more components of the test liquid. In an exemplary embodiment, the flow cell can be useful for detecting the oxidation of luciferin to oxyluciferin by the enzyme luciferase, e.g., for monitoring of a pyrosequencing reaction in one or more flow cells.

In some embodiments, the flow cell contains two, or more, optical windows. Two or more optical windows can be utilized to transmit incident light from an incident light source into the test liquid through one optical window (3), and transmit exiting photons for detection with a light detector through the second optical window (7). Exemplary techniques utilizing two or more optical windows include detection or monitoring of: fluorescence, absorbance or transmittance, polarization, refractive index, and light scattering.

In some embodiments, the optical windows are on opposite sides of the flow cell. For example, the optical windows can be positioned on opposite sides of the flow cell to permit transmission of light through the flow cell in a direction parallel to the bulk flow of liquid (8). For example, optical windows can be located at the positions described in FIGS. 1 (3) and (7). Alternatively, the optical windows can be positioned on opposite sides of the flow cell to permit transmission of light through the flow cell in a direction perpendicular to the bulk flow of liquid. For example, optical windows can be located on opposite sides of the main body (2) at the intersection of (8) and (9).

In some embodiments, two optical windows are positioned orthogonally to each other. For example, an incident light source can be transmitted through a first optical window to excite a fluorescent molecule in the test liquid, the resulting fluorescent light can be transmitted through an orthogonally positioned optical window to a detector. In some cases, the flow cell can contain an optical window for transmission of incident light, an orthogonally placed optical window for transmission of fluorescent signal, and a third optical window opposite the first for simultaneous measurement of absorbance and/or monitoring of the intensity of incident light.

The flow cell can have an inner volume having a circular, substantially circular, or non-circular cross section. Generally, circular cross-sections are preferred to minimize dead zones and areas of recirculation. In some cases, the inner volume of the flow cell has a constant cross sectional area. A flow cell having an inner volume with a constant cross sectional area and a circular cross section will form a column of constant radius FIG. 3A.

Figure 3:
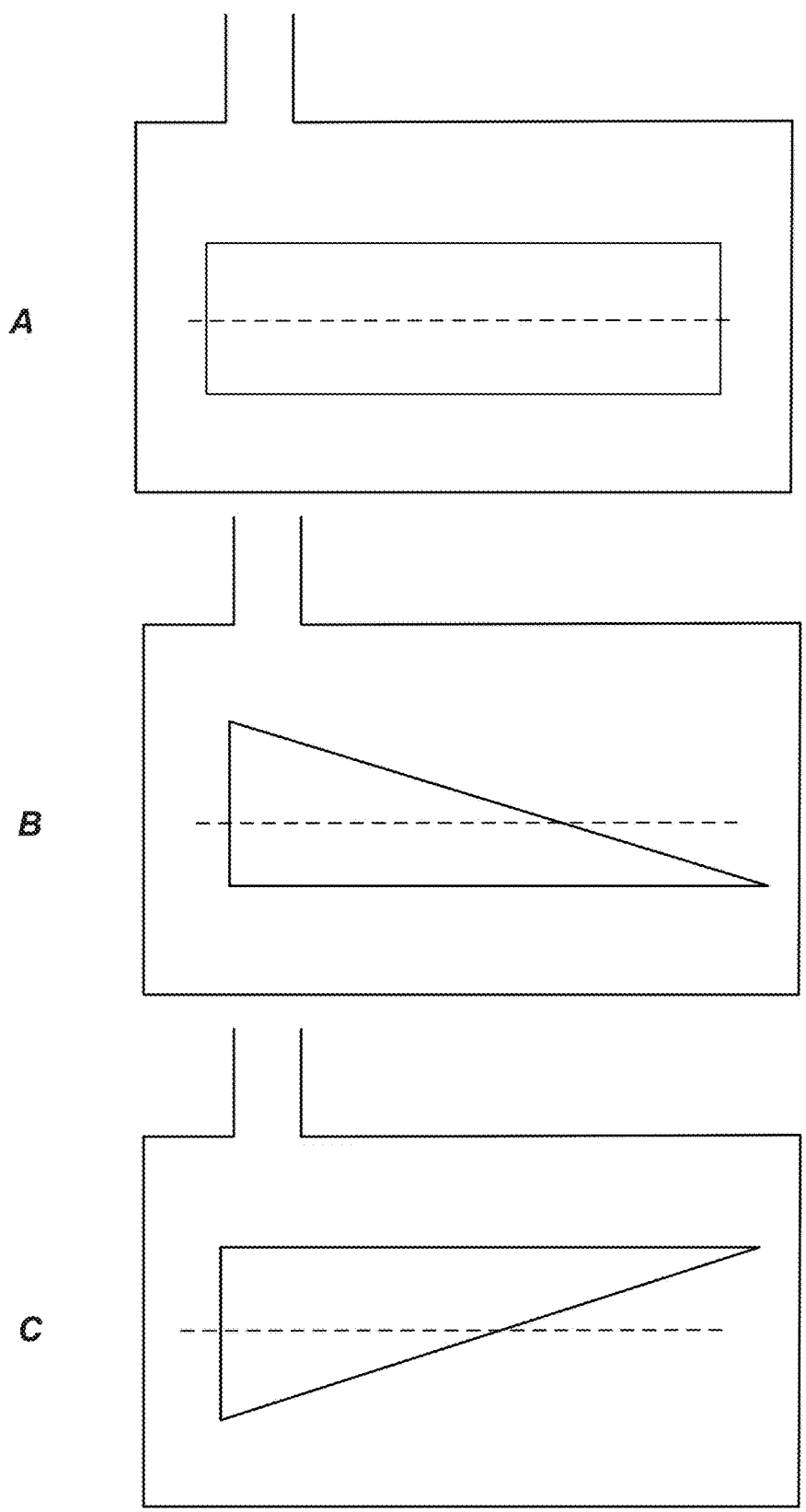
FIG. 3: Depicts side views of various flow cell geometries. A. A flow cell of constant cross sectional area. B. and C. Alternate flow cells of decreasing cross sectional area.
Figure 4:
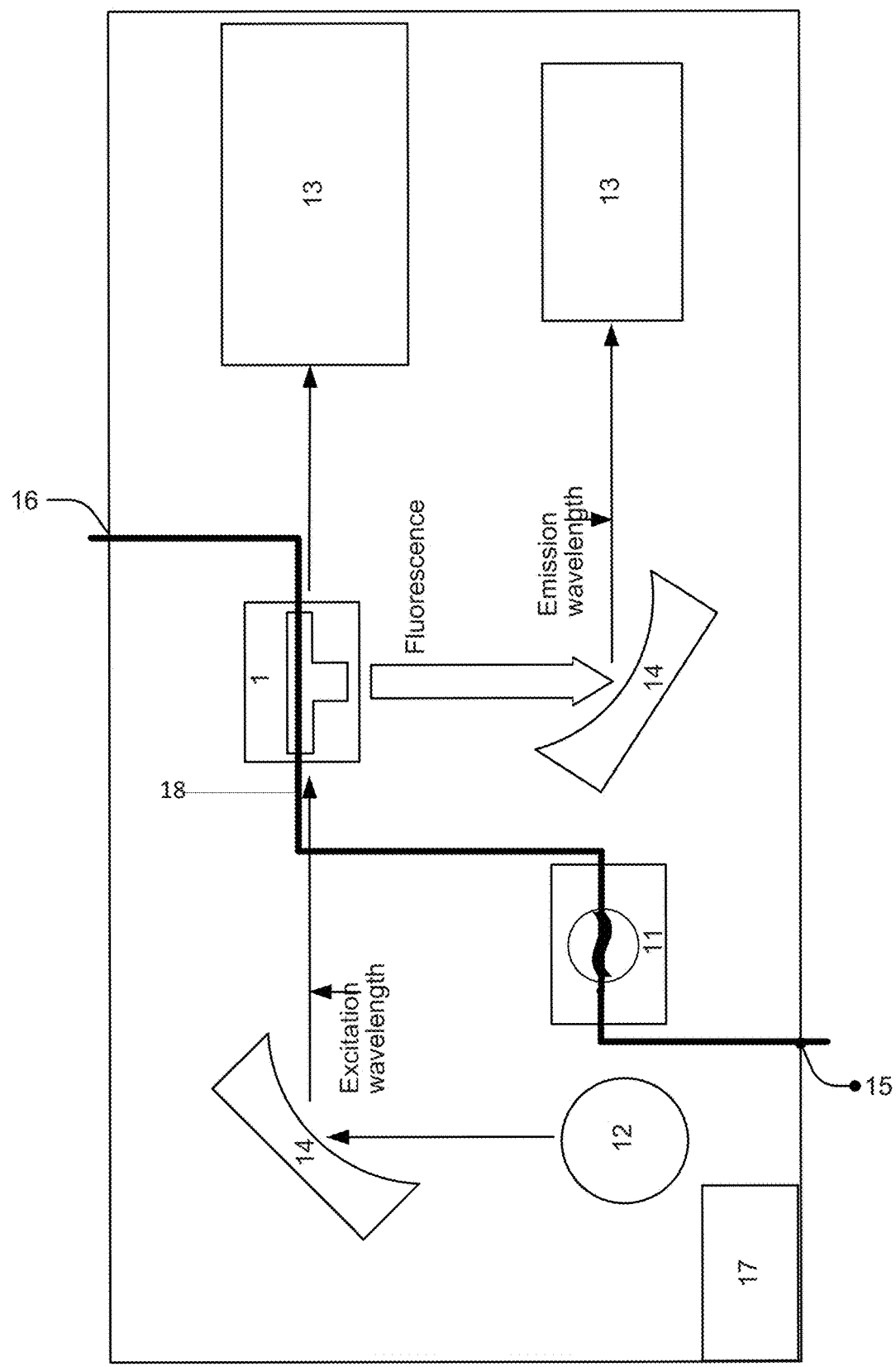
FIG. 4: Depicts a system for analysis of the fluorescence or absorbance of a test liquid with a flow cell.

In some cases, the inner volume of the flow cell has a cross sectional area that reduces from the inlet side of the flow cell to the outlet side of the flow cell. A flow cell having an inner volume cross sectional area that reduces from the inlet to the outlet forms a column of decreasing radius FIG. 1. FIGS. 3 B and C describe alternate arrangements for decreasing the volume of the flow cell from the inlet side to the outlet side.

The flow cell volume is typically small relative to the total amount of liquid that is passed through. Small flow cell volumes can reduce mixing of adjacent peaks in the flow cell and increase apparent chromatographic resolution. In some cases, the flow cell volume is configured to be approximately 5%, 10%, or 20% of the typical or expected peak volume of an analyte in a test liquid. Flow cell volumes can range from milliliters to microliters, to less than one nanoliter. Typical flow cell volumes for HPLC applications include volumes of about 2 µl, 6 µl, or 13 µl. Typical flow cell volumes for microfluidics applications include volumes ranging from less than 1 nanoliter to about 1; 5; 10; 15; 20; 25; 50; 75; 100; 150; 200; 300; 400; 500; 750; 1,000; or 1,500 nanoliters.

The flow cell can be formed of, or coated with, a material that is strongly resistant to the corrosive effects of common liquid chromatography test liquid components, including acids, bases, oxidizing agents, or reducing agents. Suitable materials include, but are not limited to one or more of borosilicate glass, fused quartz, corundum, silicon, PTFE, ETFE, PEEK, gold, platinum, or a perfluoroelastomer. In some embodiments, the flow cell is configured to inhibit or block the transmission of light through the flow cell or through the main body of the flow cell, except the portion(s) containing an optical window. For example, the flow cell, or the portion abutting one or more optical windows, can be an opaque material, such as black glass, borosilicate glass, fused quartz, or corundum; or black coated glass, borosilicate glass, fused quartz, corundum, or a polymer such as polymethylmethacrylate or polyimide. Thus, light transmission is confined to the one or more optical windows and the test liquid. Other suitable flow cell materials include, but are not limited to, various corrosion resistant metal alloys.

II. Systems

Described herein are systems for liquid chromatographic analysis (e.g., HPLC) of a test liquid. The system can contain a flow cell, such as a flow cell described herein, and one or more additional components for use of the flow cell, such as a pump (11); a light source (12); a detector (13); a mirror, a filter, and/or a diffraction grating (14); an input port (15) for injecting sample, an outlet (16); a data input port for inputting manual or computer controls; a processor (17) for processing raw data collected by a detector; and/or an output port for outputting or displaying data. Generally, the flow cell has an inlet (18) for supply of the test liquid, the inlet configured to supply a vortex flow of the test liquid through the main body of the flow cell and outlet for discharge of the test liquid from the flow cell, wherein the inlet and the outlet are on opposite sides of the main body of the flow cell. Alternatively, or additionally, the flow cell can have a larger cross sectional area on the inlet side as compared to the outlet side.

The system can contain a variety of detectors as known in the art. In a system containing a flow cell with an optical window, the system can contain one or more photon detectors. Suitable photon detectors include, but are not limited to: photomultiplier tubes, photodiodes, photodiode arrays, avalanche diodes, complementary metal oxide semiconductor based light detectors, and charged coupled devices. The system can be configured such that a photon detector is adjacent or proximal to an optical window configured to transmit light from the flow cell. In some cases, a filter or diffraction grating, or one or more mirrors can be interposed between the optical window and the photon detector. In one embodiment, the system contains an input and an output optical window, a light source positioned to transmit light through the input optical window and the test liquid and out the output optical window, and a diffraction grating interposed between the output optical window and a photodiode array for simultaneous measurement of absorbance at multiple wavelengths.

The system can also contain a light source such as a light emitting diode, a deuterium lamp, a tungsten lamp, a xenon lamp, or a combination thereof. Suitable light sources can depend on the wavelength of incident light used to analyze the test liquid. In some cases, the system is configured to interrogate the test liquid with ultraviolet light, and a deuterium lamp light source is utilized. In some cases, the system is configured to interrogate the test liquid with visible light, and a tungsten lamp light source is utilized. In some cases, the system is configured to interrogate the test liquid with a range of wavelengths spanning ultraviolet and visible light, and a combination of a deuterium and tungsten lamp light source is utilized. In some cases, the system is configured to interrogate the test liquid with a high intensity excitation source for detection of induced fluorescence, and a xenon lamp light source is utilized. The system can be configured such that a light source is adjacent or proximal to an optical window configured to transmit light into the flow cell. In some cases, a filter or diffraction grating, or one or more mirrors can be interposed between the optical window and the light source.

The system can contain one or more pumps for moving test liquid through the flow cell. Suitable pumps are known in the art and include piston pumps, peristaltic pumps, diaphragm pumps, and the like. Generally, the pump is formed of material that is resistant to the corrosive effects of the test liquid, or components therein. An exemplary pump is a piston HPLC pump with a silicon carbide or corundum piston, pump head, and/or working chamber.

II. Methods

Figure 5:
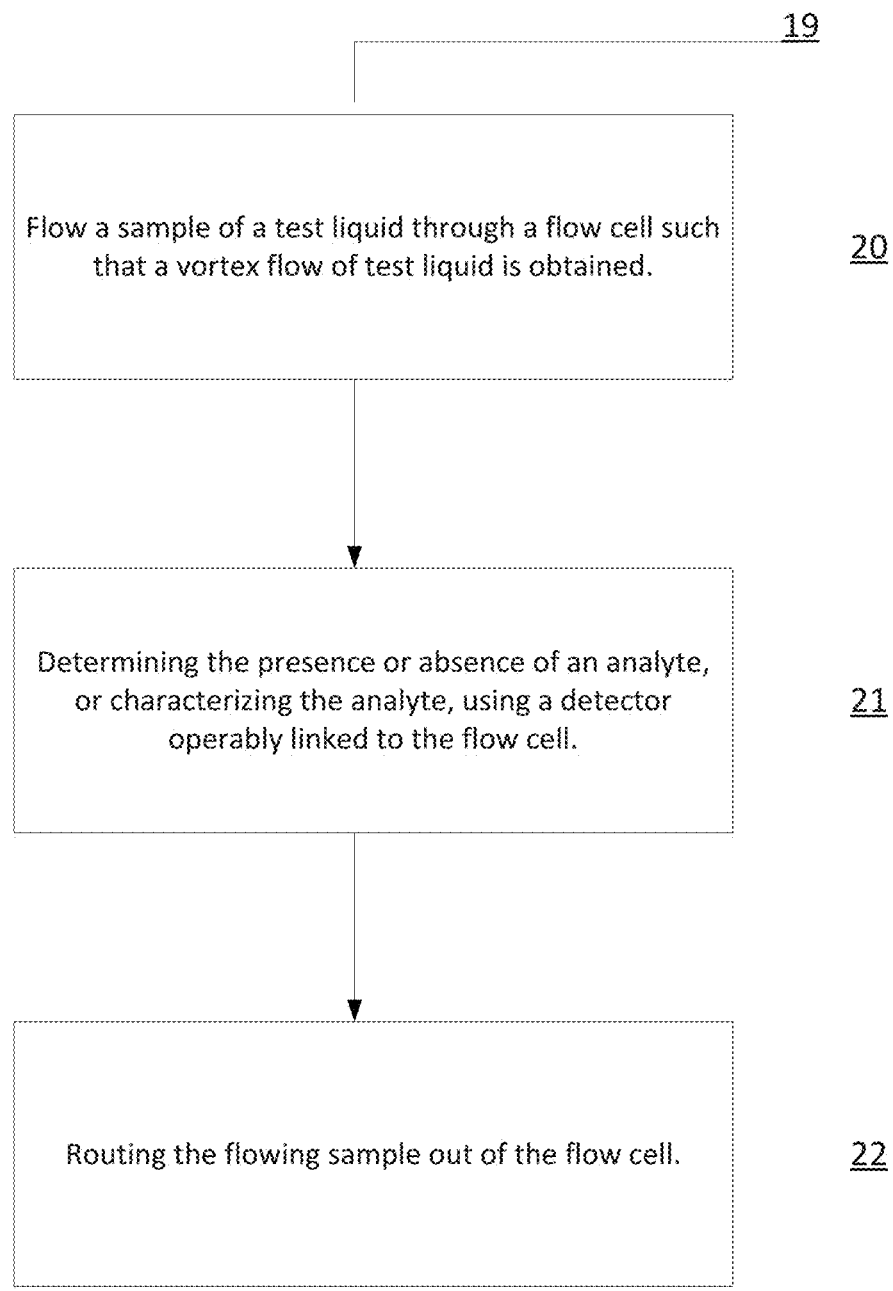
FIG. 5: Depicts a flow diagram of a method for analyzing a sample of a test liquid, according to an embodiment of the invention.
Figure 6:
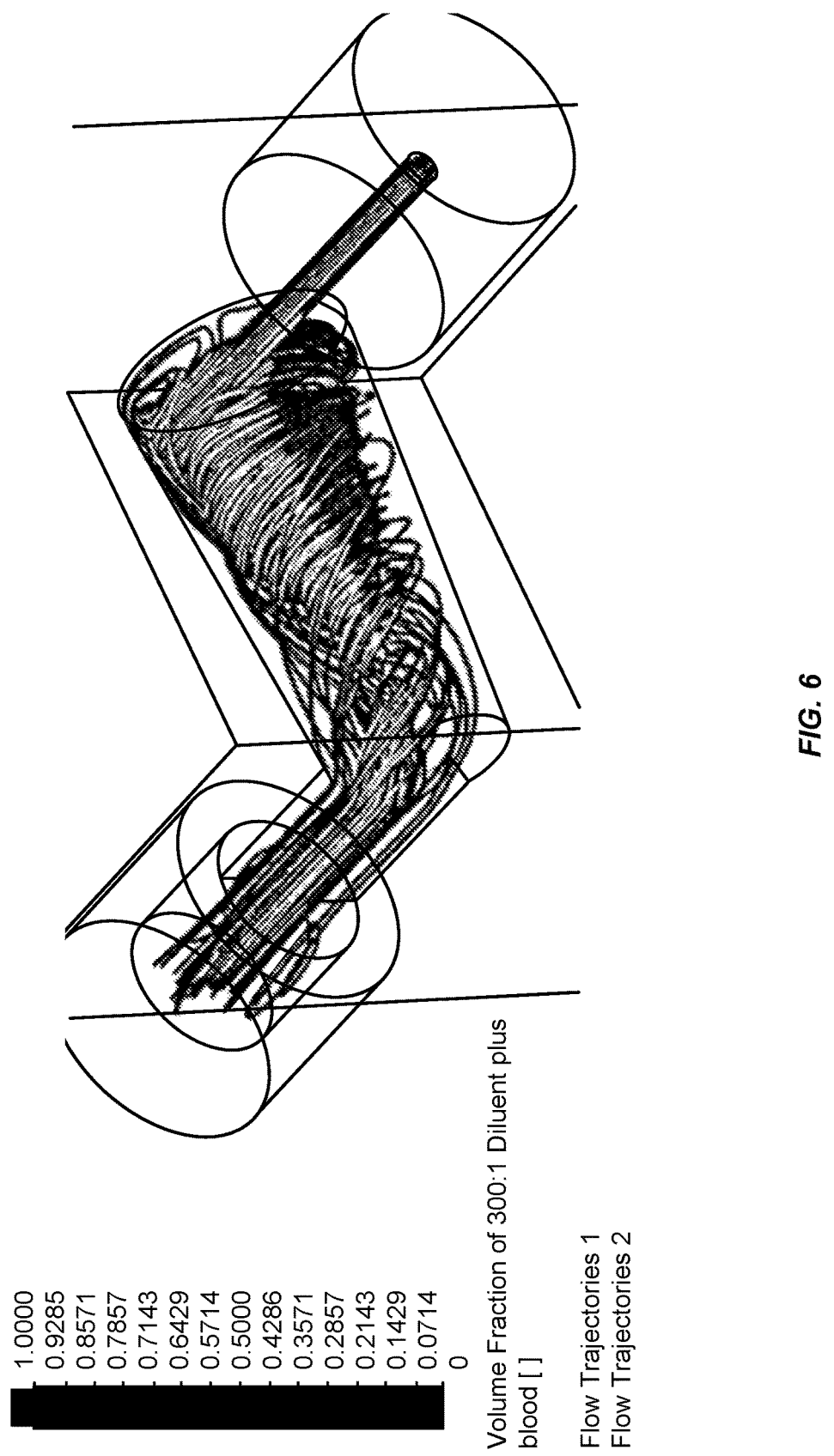
FIG. 6: Depicts a computer simulation of liquid through a flow cell of the present invention.

FIG. 5 is a flowchart illustrating a method (19) for analyzing a sample of a test liquid according to an embodiment of the present invention. At step (20), a sample is flowed through a flow cell in a manner that generates or provides a vortex flow of the test liquid through the flow cell. For example, the inlet may be positioned to inject the test liquid at a tangent relative to a circular, or substantially circular, cross sectional area of the flow cell main body. The sample is generally a liquid sample including a plurality of one or more types of analytes. As used herein, an analyte is any substance within a sample that is the subject of analysis.

In step (21), an amount of an analyte in the flowing sample passing by a fixed location, e.g., the center of the light beam, in the flow cell is determined (e.g., over a time interval) using a detector signal. The detector can be a light-absorption or transmission detector, a fluorescence detector, a conductivity detector, a refractive index detector, an electrochemical detector, or a light scattering detector. For example, light at 415 nm may be transmitted through the flow cell and absorbance of that light detected. As another example, light may be directed into the flow cell to stimulate photon emission (e.g., fluorescence) from one or more components of the test liquid, and the emitted photon detected. Accordingly, the detector can be used to aid in measuring a component of the test liquid. In some embodiments, the detector outputs a signal to a chromatography analyzer. As used herein, "signal" can comprise a single signal or a plurality of signals. The signal may be a voltage, a current, an analog, or a digital value. The determination can be based on integrating real-time light-absorption or fluorescence values of the detector signal. As the values are calculated in real-time, the amount of the analyte, which passes by the fixed location of the detector, can be determined as a function of time. In some embodiments, the calculation can be based on a real-time integration of the product of concentration and flow-rate over time. In another embodiment, this integral can be adequately approximated by summation of absorbance values measured at fixed time intervals.

Assuming a constant flow rate and a constant concentration value, the following equation may be used to determine the amount of analyte over the time interval T, where F=flow rate (vol/time) and c=concentration (mass/vol):

$$m = FcT$$

The absorptivity of the analyte may have a linear relationship with the concentration value. Thus, concentration may be replaced with the following equation, where a=absorptivity, and b=path length (distance traveled by light through the flow cell):

$$c = \frac{AU}{ab} \text{ thus, } m = F\frac{AU}{ab}T$$

In some embodiments, a variable concentration can be expressed in terms of a varying absorbance value AU by the following equation:

$$c(t) = \frac{1}{ab} A U(t)$$

Assuming a constant flow rate and a varying concentration value over time, the following integral may be used to determine the mass or amount of the analyte:

$$m = \frac{F}{ab} \int_{t_0}^{t_0+T} A U(t) dt$$

Assuming a variable flow rate and a variable concentration value over time, the following integral may be used to determine the mass or amount of the analyte:

$$m = \frac{1}{ab} \int_{t_0}^{t_0+T} F(t) A U(t) dt$$

In step (22), the sample is routed through an outlet and out of the flow cell. In some cases, a portion of the sample can be diverted without stopping the flow of the sample. For example, at the beginning of a time interval, a portion of the sample is initially diverted to a sample container; and at the end of the time interval, the sample can be rerouted back to its original flow output. In some embodiments, this diversion and rerouting is performed by switching valves at various times based on the time interval. The portion of the sample can be routed for further tests, such as HPLC or an immunoassay test.

In some embodiments, the method can include optionally changing the test liquid after supplying the test liquid into the flow cell inlet. For example, a first test liquid can be injected into the flow cell inlet to generate a vortex flow, thereby generating a vortex flow of the test liquid through the measuring chamber (e.g., main body) of the flow cell, and then a second test liquid can be injected into the flow cell inlet. The optical properties of the first and second test liquid can be measured as the test liquids flow through the flow cell. Thus the optical properties of the first and second test liquid can be compared. In some cases, the flow cells described herein provide high resolution between two test liquids so that residual first test liquid does not confound, or interferes less with, measurement of the second test liquid.

The specific details of the specific aspects of the present invention may be combined in any suitable manner without departing from the spirit and scope of embodiments of the invention. However, other embodiments of the invention may be directed to specific embodiments relating to each individual aspects, or specific combinations of these individual aspects.

It should be understood that the present invention as described above can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission. Suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices. The computer readable medium, and/or the hardware that implements the computer readable medium, can reside in the flow cell system, the raw data can then be processed in the flow cell system. Additionally, or alternatively, the flow cell can output raw data to be analyzed by hardware and software external to, e.g., operably connected to, the flow cell system.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g., a hard drive or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

EXAMPLES

Example 1

Figure 7:
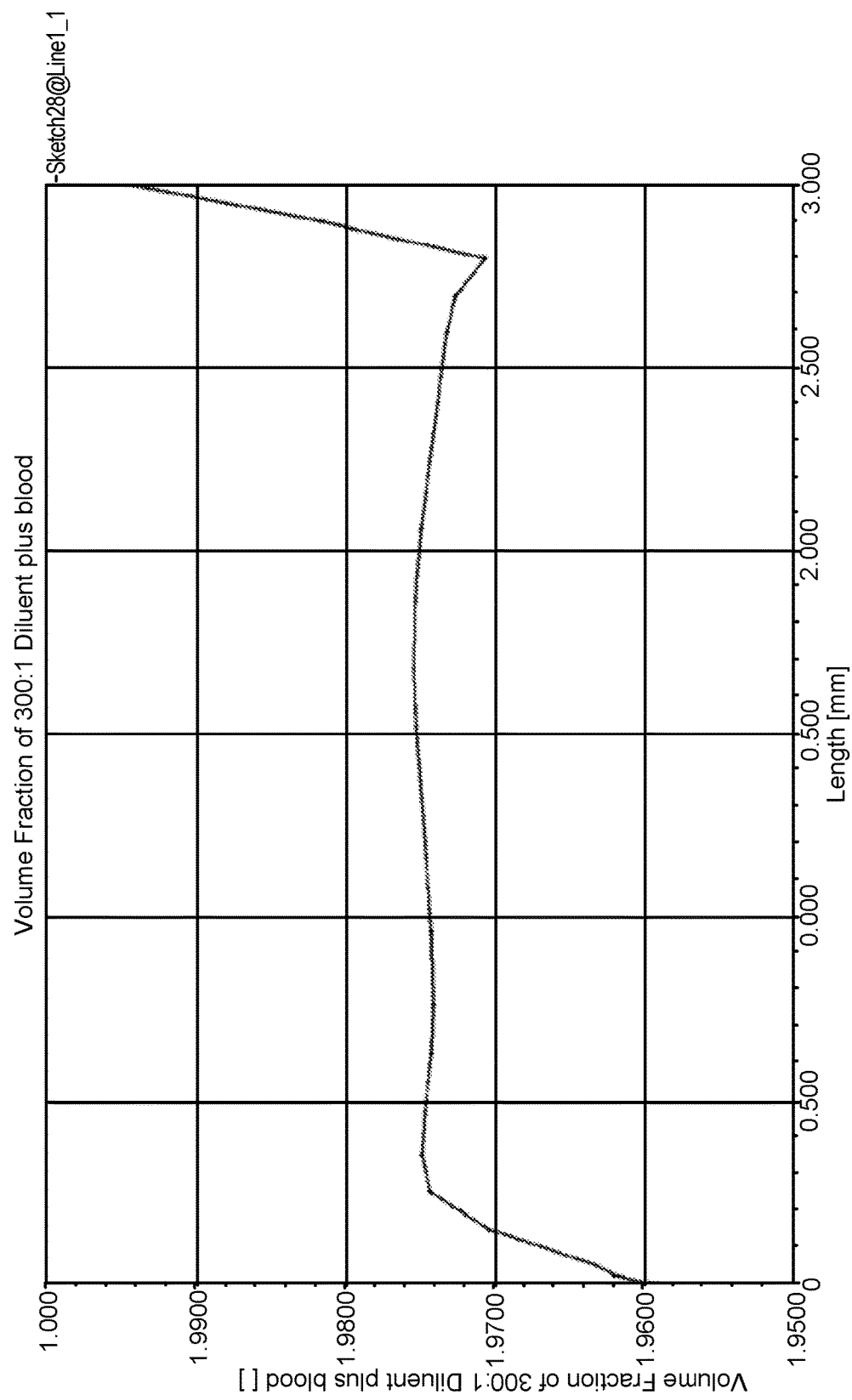
FIG. 7: Depicts a simulated sample volume profile for a flow cell with conventional inlet and outlet ports.
Figure 8:
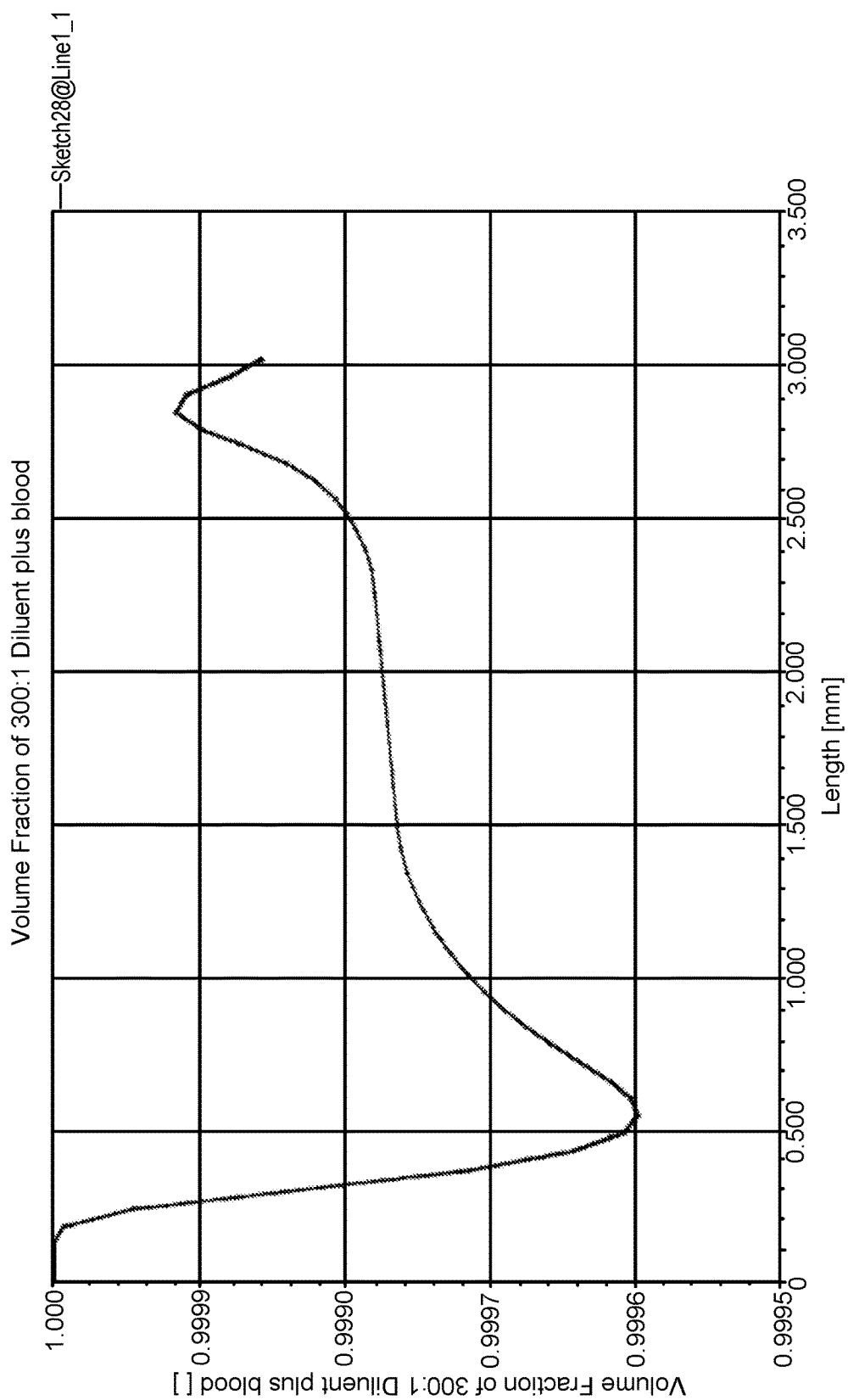
FIG. 8: Depicts a simulated sample volume profile for a flow cell of the invention.

A sample is introduced into a conventional flow cell. The sample plug width is 1 second, corresponding to 33 µL. A snapshot of the sample volume profile in the flow cell is taken 0.8 seconds after sample injection. The resulting sample volume profile is indicated in FIG. 7. As illustrated in FIG. 7, the sample is diluted by liquid in the flow cell to as low as 96% of its starting concentration. This degree of sample dilution shows poor flushing, which causes peak tailing and other problems during chromatographic analysis. For comparison, a sample is introduced into a flow cell of the present invention, under the conditions described above. The resulting sample volume profile is indicated in FIG. 8. As illustrated in FIG. 8, the sample volume ratio varies from 100% to a minimum of 99.96%, indicating very efficient filling of the flow cell only 0.8 seconds after injection.

What is claimed is:

1. A flow cell for optical analysis of a test liquid, the flow cell comprising:
   a measuring chamber;
   a first and a second optical window, the first and second optical windows on opposite sides of the measuring chamber;
   an inlet for supply of the test liquid into the flow cell, wherein the inlet is configured to supply a vortex flow of the test liquid through the measuring chamber when the test liquid is supplied through the inlet and into the flow cell; and
   an outlet for discharge of the test liquid from the flow cell, wherein the inlet and outlet are on opposite sides of the measuring chamber, wherein the cross-section of the measuring chamber has a larger surface area at the inlet side as compared to the outlet side.

2. The flow cell of claim 1, wherein the measuring chamber has a circular cross-section.

3. The flow cell of claim 1 wherein the measuring chamber has a top portion and a bottom portion, wherein the top portion slopes from the inlet to the outlet, thereby decreasing the surface area of the cross-section of the measuring chamber.

4. The flow cell of claim 1 wherein the measuring chamber has a top portion and a bottom portion, wherein the bottom portion slopes from the inlet to the outlet, thereby decreasing the surface area of the cross-section of the measuring chamber.

5. The flow cell of claim 1 wherein the measuring chamber has a top portion and a bottom portion, wherein the top portion and the bottom portions slope from the inlet to the outlet, thereby decreasing the surface area of the cross-section of the measuring chamber.

6. The flow cell of claim 1 wherein the inlet is configured to supply the test liquid at a tangent relative to (i) an inscribed circle of the inner volume of the measuring chamber; or (ii) the circular cross-section of the measuring chamber of the flow cell, when the test liquid is supplied through the inlet and into the flow cell.

7. A system comprising the flow cell of claim 1, wherein the system comprises a light detector positioned near the first optical window.

8. The system of claim 7, wherein the light detector is proximal to the inlet.

9. The system of claim 7, wherein the light detector is proximal to the outlet.

10. The system of claim 7, wherein the system comprises an incident light source positioned near the second optical window.

11. The system of claim 7, wherein the system further comprises a pump for pumping the test liquid into the inlet.

12. A method for optical analysis of a test liquid, the method comprising:
    supplying the test liquid into the flow cell inlet of the system of claim 7, thereby generating a vortex flow of the test liquid through the measuring chamber of the flow cell;
    optionally, changing the test liquid; and
    measuring the optical properties of the test liquid(s) by detecting a photon from the flow cell with the light detector.

13. The method of claim 12, wherein the detecting the photon from the flow cell with the light detector comprises detecting a photon emitted from one or more components of the test liquid after stimulation with an incident light source.

14. The method of claim 12, wherein the detecting the photon from the flow cell with the light detector comprises detecting a photon transmitted through the flow cell from the incident light sources.

15. The flow cell of claim 1 wherein the outlet has a width equal to the radius of (i) an inscribed circle of the outlet side of the measuring chamber, or (ii) the circular cross-section of the outlet side of the measuring chamber.

* * * * *